United States Patent [19]

Bird et al.

[11] Patent Number: 5,137,913
[45] Date of Patent: Aug. 11, 1992

[54] DIARYL ETHER CYCLIC ETHERS

[75] Inventors: Thomas G. C. Bird, Witry-Les-Reims, France; Philip N. Edwards, Bramhall, England

[73] Assignees: Imperial Chemical Industries PLC, London, England; ICI Pharma, Cergy, France

[21] Appl. No.: 806,775

[22] Filed: Dec. 12, 1991

Related U.S. Application Data

[63] Continuation of Ser. No. 547,161, Jul. 3, 1990, abandoned.

[30] Foreign Application Priority Data

Jul. 18, 1989 [EP] European Pat. Off. ......... 894020478

[51] Int. Cl.$^5$ ................. A61K 31/335; C07D 317/22; C07D 319/06; C07D 319/12
[52] U.S. Cl. .................................... 514/467; 549/347; 549/373; 549/374; 549/378; 549/451; 549/453; 549/30; 514/450; 514/452
[58] Field of Search .............. 549/347, 373, 374, 378, 549/451, 453; 514/450, 452, 467

[56] References Cited

U.S. PATENT DOCUMENTS

| | | |
|---|---|---|
| 3,661,917 | 5/1972 | Kalmer . |
| 4,100,296 | 7/1978 | Farooq et al. .................... 549/453 |
| 4,918,081 | 4/1990 | Huang . |
| 4,920,130 | 4/1990 | Huang . |
| 4,920,131 | 4/1990 | Huang . |
| 4,920,132 | 4/1990 | Huang . |
| 4,920,133 | 4/1990 | Huang . |

FOREIGN PATENT DOCUMENTS 0110405 6/1984 European Pat. Off. .
0181568 5/1986 European Pat. Off. .
0190722 8/1986 European Pat. Off. .
0200101 12/1986 European Pat. Off. .
0271287 6/1988 European Pat. Off. .
0349062 1/1990 European Pat. Off. .

Primary Examiner—Nicky Chan
Attorney, Agent, or Firm—Cushman, Darby & Cushman

[57] ABSTRACT

The invention concerns a diaryl ether cyclic ether of the formula I, or a pharmaceutically-acceptable salt thereof,

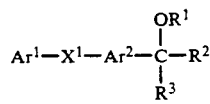

wherein
Ar$^1$ is optionally substituted phenyl or naphthyl;
X$^1$ is oxy, thio, sulphinyl or sulphonyl;
Ar$^2$ is optionally substituted phenylene, or a 6-membered heterocyclene moiety containing up to three nitrogen atoms;
R$^1$ and R$^2$ together form a group of the formula —A$^2$—X$^2$—A$^3$— wherein each of A$^2$ and A$^3$ is (1-4C) alkylene and X$^2$ is oxy, thio, sulphinyl, sulphonyl or imino; and
R$^3$ is (1-6C)alkyl, (2-6C)alkenyl, (2-6C)alkynyl and substituted (1-4C)alkyl.

The invention also concerns processes for the manufacture of a diaryl ether cyclic ether of the formula I, or a pharmaceutically-acceptable salt thereof, and pharmaceutical compositions containing said cyclic ether. The compounds of the invention are inhibitors of the enzyme 5-lipoxygenase.

8 Claims, No Drawings

DIARYL ETHER CYCLIC ETHERS

This is a continuation of application Ser. No. 07/547,161, filed on Jul. 3, 1990, now abandoned.

This invention concerns novel diaryl ether cyclic ethers and more particularly novel diaryl ether cyclic ethers which are inhibitors of the enzyme 5-lipoxygenase (hereinafter referred to as 5-LO). The invention also concerns processes for the manufacture of said diaryl ether cyclic ethers and novel pharmaceutical compositions containing said diaryl ether cyclic ethers. Also included in the invention is the use of said diaryl ether cyclic ethers in the treatment of various inflammatory and/or allergic diseases in which the direct or indirect products of 5-LO catalysed oxidation of arachidonic acid are involved, and the production of new medicaments for such use.

As stated above the diaryl ether cyclic ethers described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain diaryl ether cyclic ethers are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a diaryl ether cyclic ether of the formula I (set out hereinafter) wherein $Ar^1$ is phenyl or naphthyl which may optionally bear one or more substituents selected from amino, halogeno, hydroxy, cyano, (1–4C)alkyl, (2–4C)alkenyl, (2–4C)alkynyl, (1–4C)alkoxy, (1–4C)alkylthio, (1–4C)alkysulphinyl, (1–4C)alkylsulphonyl, (1–4C)alkylamino, di-[(1–4C)alkyl]amino, (1–4C)alkoxycarbonyl, (2–4C)alkanoyl, hydroxy-(1–4C)alkyl, fluoro-(1–4C)alkyl, cyano-(1–4C)alkyl, fluoro-(1–4C)alkoxy, cyano-(1–4C)alkoxy, phenyl and benzoyl, and wherein said phenyl or benzoyl substituents may optionally bear a substituent selected from halogeno, (1–4C)alkyl and (1–4C)alkoxy; wherein $X^1$ is oxy, thio, sulphinyl or sulphonyl; wherein $Ar^2$ is phenylene which may optionally bear one or two substituents selected from halogeno, hydroxy, amino, nitro, cyano, carbamoyl, (1–4C)alkyl, (3–4C)alkenyloxy, (1–4C)alkoxy, (1–4C)alkylthio, (1–4C)alkylsulphinyl, (1–4C)alkysulphonyl, (1–4C)alkylamino, di-[(1–4C)alkyl]amino, fluoro-(1–4C)alkyl, cyano-(1–4C)alkyl, (1–4C)alkoxycarbonyl, N-[(1–4C)alkyl]carbamoyl, N,N-di-[(1–4C)alkyl]carbamoyl, (2–4C)alkanoylamino, fluoro-(1–4C)alkoxy, cyano--(1–4C)alkoxy, carbamoyl-(1–4C)alkoxy, amino-(2–4C)alkoxy, (1–4C)alkylamino-(2–4C)alkoxy, di-[(1–4C)alkyl]amino-(2–4C)alkoxy and (1–4C)alkoxycarbonyl-(1–4C)alkoxy; or $Ar^2$ is a 6-membered heterocyclene moiety containing up to three nitrogen atoms which may optionally bear one or two substituents selected from halogeno, hydroxy, amino, cyano, (1–4C)alkyl, (1–4C)alkoxy, (1–4C)alkylamino and di-[(1–4C)alkyl]amino; wherein $R^1$ and $R^2$ together form a group of the formula $-A^2-X^2-A^3-$ which, together with the oxygen atom to which $A^2$ is attached and with the carbon atom to which $A^3$ is attached, defines a ring having 5 to 7 ring atoms, wherein $A^2$ and $A^3$, which may be the same or different, each is (1–3C)alkylene and $X^2$ is oxy, thio, sulphinyl, sulphonyl or imino, and which ring may bear one or two substituents, which may be the same or different, selected from halogeno, hydroxy, cyano, (1–4C)alkyl, (1–4C)alkoxy, (1–4C)alkylthio, (1–4C)alkylsulphinyl, (1–4C)alkylsulphonyl and fluoro-(1–4C)alkyl, or which ring may bear a (1–4C)alkylenedioxy substituent, and wherein $R^3$ is (1–6C)alkyl, (2–6C)alkenyl, (2–6C)alkynyl, fluoro-(1–4C)alkyl, cyano-(1–4C)alkyl, hydroxy-(1–4C)alkyl, (1–4C)alkoxy-(1–4C)alkyl or (2–4C)alkanoyloxy-(1–4C)alkyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms. It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for a halogeno substituent which may be present on $Ar^1$ or $Ar^2$, or on a phenyl or benzoyl substituent on $Ar^1$ is, for example, fluoro, chloro, bromo or iodo.

A suitable value for a (1–4C)alkyl substituent which may be present on $Ar^1$ or $Ar^2$, or on a phenyl or benzoyl substituent on $Ar^1$, is, for example, methyl, ethyl, propyl, isopropyl, butyl, isobutyl, sec-butyl or tert-butyl.

A suitable value for a (2–4C)alkenyl substituent on $Ar^1$ is, for example, vinyl, allyl, 2-butenyl or 3-butenyl.

A suitable value for a (2–4C)alkynyl substituent on $Ar^1$ is, for example, ethynyl, 1-propynyl, 2-propynyl, 1-butynyl or 2-butynyl.

A suitable value for a (1–4C)alkoxy substituent which may be present on $Ar^1$ or $Ar^2$ or on a phenyl or benzoyl substituent on $Ar^1$, is, for example, methoxy, ethoxy, propoxy, isopropoxy or butoxy.

Suitable values for substituents which may be present on $Ar^1$ or $Ar^2$ include, for example:
for (1–4C)alkythio: methylthio, ethylthio, propylthio, isopropylthio and butylthio;
for (1–4C)alkylsulphinyl: methylsulphinyl, ethylsulphinyl, propylsulphinyl, isopropylsulphinyl and butylsulphinyl;
for (1–4C)alkylsulphonyl: methylsulphonyl, ethylsulphonyl, propylsulphonyl, isopropylsulphonyl and butylsulphonyl.

A suitable value for a (2–4C)alkanoyl substituent which may be present on $Ar^1$ is, for example, acetyl, propionyl or butyryl.

Suitable values for substituents which may be present on $Ar^1$ or $Ar^2$ include, for example:
for (1–4C)alkylamino: methylamino, ethylamino, propylamino and butylamino;
for di-[(1–4C)alkyl]amino: dimethylamino, diethylamino and dipropylamino;
for (1–4C)alkoxycarbonyl: methoxycarbonyl, ethoxycarbonyl and tert-butoxycarbonyl;
for fluoro-(1–4C)alkyl: fluoromethyl, difluoromethyl, trifluoromethyl, 2-fluoroethyl, 2,2,2-trifluoroethyl and pentafluoroethyl;
for cyano-(1–4C)alkyl: cyanomethyl, 1-cyanoethyl, 2-cyanoethyl, 3-cyanopropyl and 2-cyanoprop-2-yl;
for cyano-(1–4C)alkoxy: cyanomethoxy, 2-cyanoethoxy and 3-cyanopropoxy;
for fluoro-(1–4C)alkoxy: trifluoromethoxy, 2,2,2-trifluoroethoxy and pentafluoroethoxy.

A suitable value for a hydroxy-(1–4C)alkyl substituent which may be present on $Ar^1$ is, for example, hydroxymethyl, 1-hydroxyethyl, 2-hydroxyethyl, 1-hydroxypropyl, 2-hydroxypropyl or 3-hydroxypropyl.

A suitable value for the number of substituents which may be present on $Ar^1$ is, for example, one, two or three.

A suitable value for $Ar^2$ when it is phenylene is, for example, 1,3-phenylene or 1,4-phenylene.

A suitable value for $Ar^2$ when it is a 6-membered heterocyclene moiety containing up to three nitrogen atoms is, for example, pyridylene, pyrimidinylene, pyridazinylene, pyrazinylene or 1,3,5-triazinylene. Conveniently $Ar^2$ when it is a 6-membered heterocyclene moiety containing up to three nitrogen atoms is, for example, 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene.

Suitable values for substituents which may be present on $Ar^2$ include, for example:
for (3–4C)alkenyloxy: allyloxy, methylallyloxy, but-2-enyloxy and but-3-enyloxy;
for N-[(1–4C)alkyl]-carbamoyl: N-methylcarbamoyl, N-ethylcarbamoyl and N-propylcarbamoyl;
for N,N-di-[(1–4C)alkyl]-carbamoyl: N,N-dimethylcarbamoyl and N,N-diethylcarbamoyl;
for (2–4C)alkanoylamino: acetamido, propionamido and butyramido;
for carbamoyl-(1–4C)alkoxy: carbamoylmethoxy, 2-carbamoylethoxy and 3-carbamoylpropoxy;
for amino-(2–4C)alkoxy: 2-aminoethoxy, 3-aminopropoxy and 4-aminobutoxy;
for (1–4C)alkylamino-(2–4C)alkoxy: 2-methylaminoethoxy, 3-methylaminopropoxy and 2-methylaminoethoxy;
for di-[(1–4C)alkyl]amino-(2–4C)alkoxy: 2-dimethylaminoethoxy, 3-dimethylaminopropoxy and 2-diethylaminoethoxy;
for (1–4C)alkoxycarbonyl-(1–4C)alkoxy: methoxycarbonylmethoxy, 2-methoxycarbonylethoxy, ethoxycarbonylmethoxy and 2-ethoxycarbonylethoxy.

A suitable value for $R^3$ when it is (1–6C)alkyl is, for example, methyl, ethyl, propyl, butyl, pentyl or hexyl.

A suitable value for $R^3$ when it is (2–6C)alkenyl is, for example, vinyl, allyl, 2-butenyl or 3-butenyl; and when it is (2–6C)alkynyl is, for example, ethynyl, 1-propynyl, 2-propynyl, 1-butynyl or 2-butynyl.

A suitable value for $R^3$ when it is cyano-(1–4C)alkyl is, for example, cyanomethyl, 2-cyanoethyl or 3-cyanopropyl; when it is fluoro-(1–4C)alkyl is, for example, fluoromethyl, difluoromethyl, trifluoromethyl, 2-fluoroethyl, 2,2,2-trifluoroethyl or pentafluoroethyl; when it is hydroxy-(1–4C)alkyl is, for example, hydroxymethyl, 1-hydroxyethyl, 2-hydroxyethyl, 1-hydroxypropyl, 2-hydroxypropyl or 3-hydroxypropyl; when it is (1–4C)alkoxy-(1–4C)alkyl is, for example, methoxymethyl, 1-methoxyethyl, 2-methoxyethyl, 1-methoxypropyl, 2-methoxypropyl, 3-methoxypropyl, ethoxymethyl, 1-ethoxyethyl, 2-ethoxyethyl, 1-ethoxypropyl, 2-ethoxypropyl or 3-ethoxypropyl; and when it is (2–4C)alkanoyloxy-(1–4C)alkyl is, for example, acetoxymethyl, 2-acetoxyethyl, 3-acetoxypropyl, propionyloxymethyl, 2-propionyloxyethyl or 3-propionyloxypropyl.

When $R^1$ and $R^2$ together form a group of the formula $-A^2-X^2-A^3-$ which together with the oxygen atom to which $A^2$ is attached and with the carbon atom to which $A^3$ is attached, defines a ring having 5 to 7 ring atoms then a suitable value for $A^2$ or $A^3$, which may be the same or different, when each is (1–3C)alkylene is, for example, methylene, ethylene or trimethylene.

Suitable values for the one or two substituents which may be present on said 5- to 7-membered ring include for example:
for halogeno: fluoro, chloro and bromo;
for (1–4C)alkyl: methyl, ethyl, propyl, isopropyl, butyl and isobutyl;
for (1–4C)alkoxy: methoxy, ethoxy, propoxy, isopropoxy and butoxy;
for (1–4C)alkylthio: methylthio, ethylthio, propylthio, isopropylthio and butylthio;
for (1–4C)alkylsulphinyl: methylsulphinyl, ethylsulphinyl, propylsulphinyl, isopropylsulphinyl and butylsulphinyl;
for (1–4C)alkylsulphonyl: methylsulphonyl, ethylsulphonyl, propylsulphonyl, isopropylsulphonyl and butylsulphonyl;
for fluoro-(1–4C)alkyl: fluoromethyl, difluoromethyl, trifluoromethyl, 2-fluoroethyl, 2,2,2-trifluoroethyl and pentafluoroethyl;
for (1–4C)alkylenedioxy: methylenedioxy and ethylenedioxy.

A suitable pharmaceutically-acceptable salt of a diaryl ether cyclic ether of the invention is, for example, an acid-addition salt of a diaryl ether cyclic ether of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a diaryl ether cyclic ether of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, diaryl ether cyclic ethers of the formula I wherein:

(a) $Ar^1$ is phenyl, naphth-1-yl or naphth-2-yl which may optionally bear one, two or three substituents selected from amino, fluoro, chloro, bromo, iodo, cyano, methyl, ethyl, isopropyl, tert-butyl, methoxy, methylthio, methylsulphinyl, methylsulphonyl, methoxycarbonyl, difluoromethyl, trifluoromethyl, 1-cyanoethyl, 2-cyanoethyl, 2-cyanoprop-2-yl and cyanomethoxy; and $X^1$, $Ar^2$, $R^1$, $R^2$ and $R^3$ have any of the meanings defined hereinbefore;

(b) $Ar^1$ is phenyl or naphth-2-yl which may optionally bear one or two substituents selected from fluoro, chloro, methyl, ethyl, isopropyl, tert-butyl, methoxy, trifluoromethyl, 2-cyanoprop-2-yl, phenyl and benzoyl, and wherein said phenyl or benzoyl substituents may optionally bear a substituent selected from chloro, methyl and methoxy; and $X^1$, $Ar^2$, $R^1$, $R^2$ and $R^3$ have any of the meanings defined hereinbefore;

(c) $X^1$ is thio, sulphinyl or sulphonyl; and $Ar^1$, $Ar^2$, $R^1$, $R^2$ and $R^3$ have any of the meanings defined hereinbefore;

(d) $Ar^2$ is 1,3-phenylene or 1,4-phenylene which may optionally bear one substituent selected from fluoro, chloro, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy; and $Ar^1$, $X^1$, $R^1$, $R^2$ and $R^3$ have any of the meanings defined hereinbefore;

(e) $Ar^2$ is 1,3-phenylene which may optionally bear a substituent selected from fluoro, chloro, bromo and trifluoromethyl; and $Ar^1$, $X^1$, $R^1$, $R^2$ and $R^3$ have any of the meanings defined hereinbefore;

(f) $Ar^2$ is 2,4-, 2,5-, 3,5- or 2,6-pyridylene or 4,6-pyrimidylene which may optionally bear one substituent selected from chloro, methyl and methoxy; and $Ar^1$, $X^1$, $R^1$, $R^2$ and $R^3$ have any of the meanings defined hereinbefore; and (g) $Ar^2$ is 3,5-pyridylene; and $Ar^1$, $X^1$, $R^1$, $R^2$ and $R^3$ have any of the meanings defined hereinbefore;

(h) $R^1$ and $R^2$ together form a group of the formula $-A^2-X^2-A^3-$ which, together with the oxygen atom to which $A^2$ is attached and with the carbon atom to which $A^3$ is attached, defines a ring having 5 to 7 ring atoms, wherein $A^2$ and $A^3$, which may be the same or different, each is methylene or ethylene and $X^2$ is oxy, and which ring may bear one or two substituents selected from fluoro, hydroxy, methyl, methoxy, ethoxy, methylthio, methylsulphinyl, methylsulphonyl, trifluoromethyl and methylenedioxy, and $R^3$ is methyl or ethyl; and $Ar^1$, $X^1$ and $Ar^2$ have any of the meanings defined hereinbefore;

(i) $R^1$ and $R^2$ together form a group of the formula $-A^2-X^2-A^3-$ which, together with the oxygen atom to which $A^2$ is attached and with the carbon atom to which $A^3$ is attached, defines a ring having 5 or 6 ring atoms, wherein $A^2$ and $A^3$, which may be the same or different, each is methylene or ethylene and $X^2$ is oxy, and which ring may bear one or two substituents selected from methyl, ethyl, propyl and isopropyl, and $R^3$ is methyl or ethyl; and $Ar^1$, $X^1$ and $Ar^2$ have any of the meanings defined hereinbefore; or a pharmaceutically-acceptable salt thereof.

A preferred compound of the invention comprises a diaryl ether cyclic ether of the formula I wherein $Ar^1$ is phenyl, naphth-1-yl or naphth-2-yl which may optionally bear one or two substituents selected from amino, fluoro, chloro, cyano, methyl, tert-butyl, methoxy, methylthio, methylsulphinyl, methylsulphonyl and 2-cyanoprop-2-yl; $X^1$ is thio, sulphinyl or sulphonyl; $Ar^2$ is 1,3-phenylene or 1,4-phenylene which may optionally bear one substituent selected from fluoro, hydroxy, amino, nitro, methoxy, methylamino, cyanomethoxy and trifluoromethyl; or $Ar^2$ is 3,5-pyridylene; $R^1$ and $R^2$ together form a group of the formula $-A^2-X^2-A^3-$ which together with the oxygen atom to which $A^2$ is attached and with the carbon atom to which $A^3$ is attached, defines a ring having 5 or 6 ring atoms, wherein $A^2$ is methylene or ethylene, $A^3$ is methylene and $X^2$ is oxy, and which ring may bear one or two substituents selected from fluoro, methyl, methoxy and trifluoromethyl, and $R^3$ is methyl or ethyl; or a pharmaceutically-acceptable salt thereof.

A further preferred compound of the invention comprises a diaryl ether cyclic ether of the formula I wherein $Ar^1$ is phenyl or naphth-2-yl which may optionally bear one or two substituents selected from fluoro, chloro, methyl, ethyl, isopropyl, tert-butyl, methoxy, trifluoromethyl, 2-cyanoprop-2-yl, phenyl and benzoyl and wherein said phenyl or benzoyl substituents may optionally bear a substituent selected from chloro, methyl and methoxy; $X^1$ is oxy, thio, sulphinyl or sulphonyl; $Ar^2$ is 1,3-phenylene which may optionally bear a substituent selected from fluoro, chloro, bromo and trifluoromethyl; or $Ar^2$ is 3,5-pyridylene; $R^1$ and $R^2$ together form a group of the formula $-A^2-X^2-A^3-$ which, together with the oxygen atom to which $A^2$ is attached and with the carbon atom to which $A^3$ is attached, defines a ring having 5 or 6 ring atoms, wherein $A^2$ and $A^3$, which may be the same or different, each is methylene or ethylene and $X^2$ is oxy, and which ring may bear one or two substituents selected from methyl, ethyl, propyl and isopropyl, and $R^3$ is methyl or ethyl; or a pharmaceutically-acceptable salt thereof.

A further preferred compound of the invention comprises a diaryl ether cyclic ether of the formula I wherein $Ar^1$ is phenyl which may optionally bear one or two substituents selected from fluoro, chloro, methyl, tert-butyl, methylthio, methylsulphinyl and 2-cyanoprop-2-yl; or $Ar^1$ is naphth-2-yl which may optionally bear a fluoro substituent; $X^1$ is thio, sulphinyl or sulphonyl; $Ar^2$ is 1,3-phenylene which may optionally bear one substituent selected from fluoro, amino, nitro, methoxy and trifluoromethyl; or $Ar^2$ is 3,5-pyridylene; $R^1$ and $R^2$ together form a group of the formula $-A^2-X^2-A^3-$ which, together with the oxygen atom to which $A^2$ is attached and with the carbon atom to which $A^3$ is attached, defines a ring having 5 or 6 ring atoms, wherein $A^2$ is methylene or ethylene, $A^3$ is methylene and $X^2$ is oxy, and which ring may bear one or two substituents selected from methyl and methoxy, and $R^3$ is methyl or ethyl; or a pharmaceutically-acceptable salt thereof.

A further preferred compound of the invention comprises a diaryl ether cyclic ether of the formula I wherein $Ar^1$ is phenyl which may optionally bear a substituent selected from fluoro, methyl, tert-butyl and phenyl; or $Ar^1$ is naphth-2-yl; $X^1$ is thio, sulphinyl or sulphonyl; $Ar^2$ is 1,3-phenylene which may optionally bear a substituent selected from fluoro, chloro, bromo and trifluoromethyl; $R^1$ and $R^2$ together form a group of the formula $-A^2-X^2-A^3$ which, together with the oxygen atom to which $A^2$ is attached and with the carbon atom to which $A^3$ is attached, defines a ring having 5 ring atoms, wherein each of $A^2$ and $A^3$ is methylene and $X^2$ is oxy, and which ring may bear one or two substituents selected from methyl, ethyl and propyl, and $R^3$ is methyl or ethyl; or a pharmaceutically-acceptable salt thereof.

A further preferred compound of the invention comprises a diaryl ether cyclic ether of the formula I wherein $Ar^1$ is 4-tert-butylphenyl, 4-(2-cyanoprop-2-yl)phenyl or naphth-2-yl; $X^1$ is thio; $Ar^2$ is 1,3-phenylene, 5-fluoro-1,3-phenylene or 5-trifluoromethyl-1,3-phenylene; $R^1$ and $R^2$ together form a group of the formula $-A^2-X^2-A^3-$ which, together with the oxygen atom to which $A^2$ is attached and with the carbon atom to which $A^3$ is attached, defines a ring having 5 ring atoms, wherein each of $A^2$ and $A^3$ is methylene and $X^2$ is oxy, and which ring bears two methyl substituents on $A^2$, and $R^3$ is ethyl; or a pharmaceutically-acceptable salt thereof.

A further compound of the invention comprises a diaryl ether cyclic ether of the formula I wherein $Ar^1$ is 4-tert-butylphenyl or naphth-2-yl; $X^1$ is thio; $Ar^2$ is 1,3-phenylene or 5-fluoro-1,3-phenylene; $R^1$ and $R^2$ together form a group of the formula $-A^2-X^2-A^3-$ which, together with the oxygen atom to which $A^2$ is attached and with the carbon atom to which $A^3$ is attached, defines a ring having 5 ring atoms, wherein each of $A^2$ and $A^3$ is methylene and $X^2$ is oxy, and which ring bears on $A^2$ two substituents, which may be the same or different, selected from methyl, ethyl and propyl; or a pharmaceutically-acceptable salt thereof.

Specific especially preferred compounds of the invention include, for example, the following diaryl ether cyclic ethers of the formula I, or pharmaceutically-acceptable salts thereof: 4-ethyl-2,2-dimethyl-4-[3-(naphth-2-ylthio)phenyl]-1,3-dioxolane, 4-ethyl-2,2-dimethyl-4-[3-(4-tert-butylphenylthio)phenyl]-1,3-dioxolane, (+)-2,4-diethyl-4-[5-fluoro-3-(naphth-2-ylthio)phenyl]-2-methyl-1,3-dioxolane (the more polar isomer) and (+)-4-ethyl-4-[5-fluoro-3-(naphth-2-ylthio)phenyl]-2-methyl-2-propyl-1,3-dioxolane (the more polar isomer).

According to a further aspect the invention there is provided a diaryl ether cyclic ether of the formula I (set out hereinafter) wherein $Ar^1$ is phenyl or naphthyl which may optionally bear one or more substituents selected from amino, halogen, hydroxy, cyano, (1-4C)alkyl, (2-4C)alkenyl, (2-4C)alkynyl, (1-4C)alkoxy, (1-4C)alkylthio, (1-4C)alkysulphinyl, (1-4C)alkylsulphonyl, (1-4C)alkylamino, di-[(1-4C)alkyl]amino, (1-4C)alkoxycarbonyl, (2-4C)alkanoyl, hydroxy-(1-4C)alkyl, fluoro-(1-4C)alkyl, cyano-(1-4C)alkyl, fluoro-(1-4C)alkoxy and cyano-(1-4C)alkoxy; wherein $X^1$ is oxy, thio, sulphinyl or sulphonyl; wherein $Ar^2$ is phenylene which may optionally bear one or two substituents selected from halogeno, hydroxy, amino, nitro, cyano, carbamoyl, (1-4C)alkyl, (3-4C)alkenyloxy, (1-4C)alkoxy, (1-4C)alkylthio, (1-4C)alkylsulphinyl, (1-4C)alkysulphonyl, (1-4C)alkylamino, di-[(1-4C)alkyl]amino, fluoro-(1-4C)alkyl, cyano-(1-4C)alkyl, (1-4C)alkoxycarbonyl, N-[(1-4C)alkyl]carbamoyl, N,N-di-[(1-4C)alkyl]carbamoyl, (2-4C)alkanoylamino, fluoro-(1-4C)alkoxy, cyano-(1-4C)alkoxy, carbamoyl-(1-4C)alkoxy, amino-(2-4C)alkoxy, (1-4C)alkylamino-(2-4C)alkoxy, di-[(1-4C)alkyl]amino-(2-4C)alkoxy and (1-4C)alkoxycarbonyl-(1-4C)alkoxy; or $Ar^2$ is a 6-membered heterocyclene moiety containing up to three nitrogen atoms which may optionally bear one or two substituents selected from halogeno, hydroxy, amino, cyano, (1-4C)alkyl, (1-4C)alkxoy, (1-4C)alkylamino and di-[(1-4C)alkyl]amino; wherein $R^1$ and $R^2$ together form a group of the formula $-A^2-X^2-A^3-$ which, together with the oxygen atom to which $A^2$ is attached and with the carbon atom to which $A^3$ is attached, defines a ring having 5 to 7 ring atoms, wherein $A^2$ and $A^3$, which may be the same or different, each is (1-3C)alkylene and $X^2$ is oxy, thio, sulphinyl, sulphonyl or imino, and which ring may bear one or two substituents, which may be the same or different, selected from halogeno, hydroxy, cyano, (1-4C)alkyl, (1-4C)alkoxy, (1-4C)alkylthio, (1-4C)alkylsulphinyl, (1-4C)alkylsulphonyl and fluoro-(1-4C)alkyl, or which ring may bear a (1-4C)alkylenedioxy substituent, and wherein $R^3$ is (1-6C)alkyl, (2-6C)alkenyl, (2-6C)alkynyl, fluoro-(1-4C)alkyl, cyano-(1-4C)alkyl, hydroxy-(1-4C)alkyl, (1-4C)alkoxy-(1-4C)alkyl or (2-4C)alkanoyloxy-(1-4C)alkyl; or a pharmaceutically-acceptable salt thereof.

A compound of the invention comprising a diaryl ether cyclic ether of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Ar^1$, $X^1$, $Ar^2$, $R^1$, $R^2$ and $R^3$ have any of the meanings defined hereinbefore.

(a) The coupling, in the presence of a suitable base, of a compound of the formula $Ar^1-X^1-H$ with a compound of the formula II wherein Z is a displaceable group; provided that, when there is an amino, imino, alkylamino or hydroxy group in $Ar^1$, $Ar^2$, $R^1$, $R^2$ or $R^3$ any amino, imino, alkylamino or hydroxy group may be protected by a conventional protecting group or alternatively any such group need not be protected; whereafter any undesired protecting group in $Ar^1$, $Ar^2$, $R^1$, $R^2$ or $R^3$ is removed by conventional means.

A suitable displaceable group Z is, for example, a halogeno or sulphonyloxy group, for example a chloro, bromo, iodo, methanesulphonyloxy or toluene-p-sulphonyloxy group.

A suitable base for the coupling reaction is, for example, an alkali or alkaline earth metal carbonate, (1-4C)alkoxide, hydroxide or hydride, for example sodium carbonate, potassium carbonate, sodium ethoxide, sodium butoxide, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

A suitable protecting group for an amino, imino or alkylamino group is, for example, an acyl group for example a (1–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (1–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula $Ar^1$—$X^1$—H and of the formula II may be obtained by standard procedures of organic chemistry. The preparation of examples of such starting materials is described within the accompanying non-limiting Examples which are provided for the purpose of illustration only. Other necessary starting materials are obtainable by analogous procedures to those described or by modifications thereto which are within the ordinary skill of an organic chemist.

Conveniently intermediates of the formula II wherein Z, $Ar^2$, $R^1$, $R^2$ and $R^3$ have the meanings defined hereinbefore, may be obtained by way of compounds of the formula Z—$Ar^2$—Y, wherein Z and $Ar^2$ have the meanings defined hereinbefore and Y is, for example, a halogeno, formyl, alkanoyl, nitrile or alkoxycarbonyl group, as illustrated in accompanying Scheme I (set out hereinafter). Thus, for example, in the accompanying non-limiting Examples it is shown how to convert a compound of the formula Z—Ar—Y wherein Y is a halogeno group to a compound of the formula II.

It will also be appreciated that the intermediate of the formula II may conveniently be obtained from the compound of the formula Z—$Ar^2$—Y, as defined hereinbefore; by reversing the order of introduction of the groups $R^2$ and $R^3$ which is used in Scheme I.

(b) The coupling, in the presence of a suitable base as defined hereinbefore, of a compound of the formula III with a compound of the formula $Ar^1$—Z wherein Z is a displaceable group as defined hereinbefore; provided that, when there is an amino, imino, alkylamino or hydroxy group in $Ar^1$, $Ar^2$, $R^1$, $R^2$ or $R^3$, any amino, imino, alkylamino or hydroxy group may be protected by a conventional protecting group as defined hereinbefore or alternatively any such group need not be protected; whereafter any desired protecting group in $Ar^1$, $Ar^2$, $R^1$, $R^2$ or $R^3$ is removed by conventional means.

The coupling reaction is conveniently performed in a suitable inert solvent as defined hereinbefore and at a temperature in the range, for example, 10° to 200° C., conveniently in the range 70° to 150° C. The reaction may conveniently be performed in the presence of a suitable catalyst as defined hereinbefore.

The starting materials of the formula $Ar^1$—Z and of the formula III may be obtained by standard procedures of organic chemistry. Such starting materials are obtainable by analogous procedures to those illustrated in accompanying Scheme II (set out hereinafter) or by modifications thereto which are within the ordinary skill of an organic chemist.

A suitable protecting group $R^4$, as employed in Scheme II, is any one of the many such groups known in the art and includes any appropriate protecting group as defined hereinbefore. Examples of such groups are given in Scheme II. The conditions for the introduction and removal of such protecting groups are described in standard textbooks of organic chemistry such as, for example, "Protective Groups in Organic Synthesis" by T W Green (J Wiley and Sons, 1981).

(c) The cyclisation, in the presence of a suitable acid, of a compound of the formula IV upon reaction with an appropriate aldehyde or with an appropriate ketone, or with the corresponding hemiacetal or acetal derivatives thereof, provided that, when there is an amino, alkylamino or hydroxy group in $Ar^1$, $Ar^2$ or $R^3$, any amino, alkylamino or hydroxy group is protected by a conventional protecting group; whereafter any undesired protecting group in $Ar^1$, $Ar^2$ or $R^3$ is removed by conventional means.

A suitable acid for the cyclisation reaction is, for example, an inorganic acid such as hydrochloric, sulphuric or phosphoric acid, or, for example, an organic acid such as p-toluenesulphonic acid or trifluoroacetic acid. The cyclisation reaction is conveniently performed in a suitable inert solvent or diluent, for example 1,2-dimethoxyethane or tetrahydrofuran. Preferably the reaction is performed using the appropriate aldehyde or ketone as both a reactant and diluent. The cyclisation is effected at a temperature in the range, for example, 20° to 150° C., conveniently at or near the boiling point of the diluent or solvent.

The tertiary alcohol starting material of the formula IV may be obtained by standard procedures of organic chemistry. The preparation of examples of such starting materials is described within the accompanying non-limiting Examples which are provided for the purpose of illustration only. Other necessary starting materials are obtainable by analogous procedures to those described or by modifications thereof which are within the ordinary skill of an organic chemist.

Conveniently intermediates of the formula $Ar^1$—$X^1$—$Ar^2$—Q, wherein $Ar^1$, $X^1$ and $Ar^2$ have the meanings defined hereinbefore and Q is, for example, a halogeno, formyl, ketone or nitrile group may be utilised in the preparation of the tertiary alcohol starting material of the formula IV using analogous procedures to those illustrated in Schemes I and II.

(d) The cyclisation, in the presence of a suitable base as defined hereinbefore, of a compound of the formula IV by reaction with a compound of the formula Z—$A^2$—Z, wherein $A^2$ and Z have the meanings defined hereinbefore, provided that, when there is an amino, alkylamino or hydroxy group in $Ar^1$, $X^1$, $Ar^2$ or $R^3$, any amino, alkylamino or hydroxy group in protected by a conventional protecting group; whereafter any undesired protecting group in $Ar^1$, $X^1$, $Ar^2$ or $R^3$ is removed by conventional means.

(e) For the production of those compounds of the formula I wherein $Ar^1$ or $Ar^2$ bears an alkylsulphinyl or alkylsulphonyl substituent; wherein $X^1$ is a sulphinyl or sulphonyl group; or wherein $R^1$ and $R^2$ together form a group of the formula —$A^2$—$X^2$—$A^3$— and $X^2$ is a sulphinyl or sulphonyl group, and which may bear one or two alkylsulphinyl or alkylsulphonyl groups; the oxidation of a compound of the formula I wherein $Ar^1$ or $Ar^2$ bears an alkylthio substituent; wherein $X^1$ is a thio group; or wherein $R^1$ and $R^2$ together form a group of the formula —$A^2$—$X^2$—$A^3$— and $X^2$ is a thio group, and which may bear one or two alkylthio groups.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(f) For the production of those compounds of the formula I wherein $Ar^2$ bears an alkanoylamino substituent, the acylation of a compound of the formula I wherein $Ar^2$ bears an amino substituent.

A suitable acylating agent is, for example, any agent known in the art for the acylation of amino to acylamino, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or tert-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae III and IV and these are provided as a further feature of the invention.

As stated previously, the cyclic ethers of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512-11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, *Brit. J. Pharmacol.* 1985, 84, 34P) which involves the use of a protein-$LTB_4$ conjugate produced using the procedure of Young et alia (*Prostaglandins*, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983. 32, 2319–2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431–438). This test provides an in vivo model for 5-LO inhibitors administered topically or orally.

f) An in vivo system involving measuring the effects of a test compound administered orally or intravenously on a leukotriene dependent bronchoiconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (*British J Pharmacology*, 1983, 78(1), 67–574). This test provides a further in vivo test for detecting 5-LO inhibitors.

g) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days). At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–f):

Test a): $IC_{50}$ in the range, for example, 0.01–30 $\mu M$;

Test b): $IC_{50}$ ($LTB_4$) in the range, for example, 0.01–40 $\mu M$, $IC_{50}$ ($TxB_2$) in the range, for example, 40–200 $\mu M$;

Test c): oral $ED_{50}$ ($LTB_4$) in the range, for example, 1–100 mg/kg;

Test d): $IC_{50}$ ($LTC_4$) in the range, for example 0.001–1 $\mu M$, $IC_{50}$ ($PGE_2$) in the range, for example, 20–1000 $\mu M$;

Test e): inhibition of inflammation in the range, for example, 0.3–100 $\mu g$ intradermally;

Test f): $ED_{50}$ in the range, for example, 0.5–10 mg/kg i.v.;

Test g): oral $ED_{50}(LTD_4)$ in the range, for example, 0.5–50 mg/kg.

No overt toxicity or other untoward effects are present in tests c), e), f) and/or g) when compounds of the formula I are administered at several multiples of their minimum inhibitory dose or concentration.

Thus, by way of example, the compound 4-ethyl-2,2-dimethyl-4-[3-(naphth-2-ylthio)phenyl]-1,3-dioxolane has an $IC_{50}$ of 0.5 $\mu M$ against $LTB_4$ in test b), and an oral $ED_{50}$ of 3 mg/kg versus $LTB_4$ in test c). In general those compounds of the formula I which are particularly preferred have an $IC_{50}$ of $<1$ $\mu M$ against $LTB_4$ in test b), and an oral $ED_{50}$ of $<100$ mg/kg against $LTB_4$ in test c).

These compounds are examples of cyclic ethers of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a cyclic ether of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is a diaryl ether cyclic ether of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a diaryl ether cyclic ether of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a cyclic ether of the formula I will naturally vary according to the nature and severity of the conditions, the age and sex of the animal or patient and the route of administration, according to well known principles of medicine. As mentioned above, diaryl ether cyclic ethers of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a diaryl ether cyclic ether of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°-25° and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

| (viii) | the following abbreviations have been used: |
|---|---|
| THF | tetrahydrofuran; |
| DMSO | dimethylsulphoxide; |
| DMF | N,N-dimethylformamide; |
| DMA | N,N-dimethylacetamide; |

(ix) the specific rotation, $[\alpha]^t$ of plane polarised light was determined using the sodium D line (5890 Angstroms), at 20° C., and generally using sample concentrations of approximately 1 g/100 ml.

EXAMPLE 1

A mixture of 2-[3-(naphth-2-ylthio)phenyl]butane-1,2-diol (2 g), 2,2-dimethoxypropane (2 g), p-toluenesulphonic acid (0.05 g) and acetone (20 ml) was heated to reflux for 45 minutes. The mixture was evaporated and the residue was purified by column chromatography using increasingly polar mixtures of hexane and ethyl acetate as eluent. There was thus obtained 4-ethyl-2,2-dimethyl-4-[3-(naphth-2-ylthio)phenyl]-1,3-dioxolane (1.1 g, 50%) as an oil.

NMR Spectrum (CDCl$_3$, δvalues) 0.8 (t, 3H), 1.25 (s, 3H), 1.5 (s, 3H), 1.8 (m, 2H), 4.05 (q, 2H), 7.2–7.5 (m, 7H), 7.6–7.8 (m, 4H).

The butane-1,2-diol used as a starting material was obtained as follows:

A mixture of 2-naphthalenethiol (3.2 g), 3-iodobromobenzene (6.7 g), potassium carbonate (1.4 g), cuprous chloride (0.4 g) and DMF (4 ml) was heated to reflux for 1 hour. The mixture was allowed to cool to ambient temperature and was partitioned between diethyl ether and water. The mixture was filtered and the organic layer was separated, dried (MgSO$_4$) and evaporated. The residue was taken up in ethyl acetate, decolourised by treatment with charcoal, reisolated and purified by recrystallisation from methanol to give 3-bromophenyl 2-naphthyl sulphide (3.9 g, 65%), m.p. 68°-70° C.

A solution of a portion (2 g) of the product so obtained in THF (8 ml) was cooled to −78° C. and n-butyl-lithium (1.6M in hexane; 3.9 ml) was added dropwise. The mixture was stirred at −78° C. for 30 minutes and a solution of 1-(tert-butyldimethylsilyloxy)butan-2-one (1.2 g) in THF (2 ml) was added. The mixture was stirred at −78° C. for 30 minutes and then allowed to warm to ambient temperature. The mixture was poured into water (50 ml) and extracted with diethyl ether (2×25 ml). The combined extracts were dried (MgSO$_4$) and evaporated to give 1-(tert-butyldimethylsilyloxy)-2-(3-(naphth-2-ylthio)phenyl)butan-2-ol.

A mixture of the product so obtained, potassium fluoride (2 g) and DMF (10 ml) was heated to 80° C. for 1 hour. The mixture was poured into water (50 ml) and extracted with diethyl ether (2×50 ml). The combined extracts were washed with water, dried (MgSO$_4$) and evaporated. The residue was purified by column chromatography using increasingly polar mixtures of hexane and ethyl acetate as eluent to give the required starting material (2 g) as an oil.

The 1-(tert-butyldimethylsilyloxy)butan-2-one used as a starting material above was obtained as follows:

1-Hydroxybutan-2-one (8.8 g) was added to a mixture of tert-butyldimethylsilyl chloride (15 g), imidazole (13.6 g) and DMF (50 ml) and the mixture was allowed to stand at ambient temperature for 18 hours. The mixture was poured into water (200 ml) and extracted with diethyl ether (2×150 ml). The combined extracts were dried (MgSO$_4$) and evaporated to give the required starting material as an oil (20 g).

EXAMPLE 2

Sodium metaperiodate (0.5 g) was added to a mixture of 4-ethyl-2,2-dimethyl-4-[3-(naphth-2-ylthio)phenyl]-1,3-dioxolane (0.5 g), ethanol (5 ml) and water (5 ml) and the mixture was stirred at ambient temperature for 24 hours. The mixture was concentrated by evaporation and the residue was partitioned between methylene chloride and water. The organic phase was dried (MgSO$_4$) and evaporated. The residue was purified by column chromatography using increasingly polar mixtures of hexane and ethyl acetate as eluent. There was thus obtained 4-ethyl-2,2-dimethyl-4-[3-(naphth-2-ylsulphinyl)phenyl]-1,3-dioxolane (0.35 g, 67%) as an oil.

NMR Spectrum (CDCl$_3$, δ values) 0.72 and 0.75 (2 t's, 3H), 1.15 and 1.2 (2 s's, 3H), 1.46 and 1.46 (2 s's, 3H), 1.85 (m, 2H), 4.08 and 4.09 (q, 2H), 7.3-8.3 (m, 11H).

EXAMPLE 3

Using a similar procedure to that described in Example 1, except that 2-[3-(naphth-2-ylsulphonyl)phenyl]butane-1,2-diol was used in place of 2-[3-(naphth-2-ylthio)phenyl]butane-1,2-diol, there was thus obtained 4-ethyl-2,2-dimethyl-4-[3-(naphth-2-ylsulphonyl)-phenyl]-1,3-dioxolane in 15% yield as an oil.

NMR Spectrum (CDCl$_3$, δ values 0.75 (t, 3H), 1.22 (s, 3), 1.5 s, 3H), 1.85 (m, 2H), 4.08 (doublet of doublets, 2H), 7.42-7.68 (m, 4H), 7.8-8.05 (m, 6H), 8.56 (m, 1H).

The 2-[3-(naphth-2-ylsulphonyl)phenyl]butane-1,2-diol used as a starting material was obtained as follows:

A solution of potassium peroxymonosulphate (17.7 g) in water (30 ml) was added to a mixture of 3-bromophenyl 2-naphthyl sulphide (3 g) and ethanol (30 ml) which had been cooled to 0° C. in an ice-bath. The mixture was stirred at ambient temperature for 18 hours and at 60° C. for 5 hours. The mixture was cooled to ambient temperature and partitioned between chloroform and water. The organic phase was dried (MgSO$_4$) and evaporated to give 3-bromophenyl 2-naphthyl sulphone (2.7 g, 82%) as a solid which was used without further purification.

Using a similar procedure to that described in the second and third paragraphs of the portion of Example 1 which is concerned with the preparation of starting materials the product so obtained was reacted with 1-(tert-butyldimethylsilyloxy)butan-2-one and the resultant product was treated with potassium fluoride. There was thus obtained the required starting material as an oil in 30% yield.

EXAMPLE 4

A mixture of (+)-2-[5-fluoro-3-(naphth-2-ylthio)-phenyl]butane-1,2-diol (0.4 g), butan-2-one (4 ml) and sulphuric acid (concentrated, 1 drop) was stirred at ambient temperature for 16 hours. Diethyl ether (30 ml) was added and the mixture was washed with aqueous sodium bicarbonate solution (5% w/v) and with brine, dried (MgSO$_4$) and evaporated. The residue was purified by column chromatography using a 11:9 v/v mixture of petroleum ether (b.p. 40°-60° C.) and toluene as eluent. There was thus obtained: a less polar isomer, (+)-2,4-diethyl-4-[5-fluoro-3-(naphth-2-ylthio)phenyl]-2-methyl-1,3-dioxolane, in 43% yield as an oil, NMR Spectrum (CDCl$_3$, δ values), 0.75 (t, 3H), 0.95 (t, 3H), 1.2 (s, 3H), 1.5-2.0 (m, 4H), 4.0 (s, 2H), 6.75-7.2 (m, 3H), 7.3-8.0 (m, 7H), [α]$^{20}$= +12.4 (chloroform, c=1 g/100 ml); and a more polar isomer in 33% yield as an oil, NMR Spectrum (CDCl$_3$, δ values) 0.75 (t, 3H), 0.8 (t, 3H), 1.4 (s, 3H), 1.55 (s, 2H), 1.6-2.0 (m, 2H), 4.0 (q, 2H), 6.75-7.1 (m, 3H), 7.3-8.0 (m, 7H), [α]$^{20}$= +11.8 (chloroform, c=1.2 g/100 ml).

The (+)-2-[5-fluoro-3-(naphth-2-ylthio)phenyl]butane-1,2-diol used as a starting material was obtained as follows:

A solution of 2-naphthalenethiol (25 g) in DMA (30 ml) was added dropwise to a stirred suspension of sodium hydride (60% w/w dispersion in mineral oil; 6.25 g) in DMA (120 ml) which had been cooled to 0° C. The mixture was stirred and allowed to warm to ambient temperature. A solution of 3,5-difluorobromobenzene (18 ml) in DMA (15 ml) was added and the mixture was heated to 60° C. for 3 hours. The mixture was cooled to ambient temperature and partitioned between diethyl ether and water. The organic phase was washed with brine, dried (MgSO$_4$) and evaporated. The residue was purified by column chromatography using petroleum ether (b.p. 40°-60° C.) as eluent. There was thus obtained 3-bromo-5-fluorophenyl naphth-2-yl sulphide in 47% yield as an oil.

NMR Spectrum (CDCl$_3$, δ values) 6.7-7.2 (m, 3H), 7.4-7.6 (m, 3H), 7.7-8.0 (m, 4H).

A Grignard reagent was prepared by heating a mixture of the product so obtained (15 g), magnesium (1.08 g), diethyl ether (45 ml) and a crystal of iodine to 40° C. for 1 hour. A solution of methyl 2-oxobutyrate (5.2 g) in diethyl ether (40 ml) was added and the mixture was stirred at ambient temperature for 1 hour. The mixture was partitioned between diethyl ether and a saturated aqueous ammonium chloride solution. The organic phase was washed with brine, dried (MgSO$_4$) and evaporated. The residue was purified by column chromatography using a 3:2 v/v mixture of petroleum ether (b.p. 40°-60° C.) and methylene chloride as eluent. There was thus obtained methyl 2-[5-fluoro-3-(naphth-2-ylthio)phenyl]-2-hydroxybutyrate in 44% yield as an oil, NMR Spectrum (CDCl$_3$, δ values) 0.9 (t, 3H), 1.7-2.2 (m, 2H), 3.7 (s, 3H), 6.85 (doublet of triplets, 1H), 7.2 (m, 1H), 7.35 (t, 1H), 7.4-7.9 (m, 7H).

A mixture of the product so obtained (6 g), potassium carbonate (2.21 g), water (13 ml) and methanol (150 ml) was heated to reflux for 1 hour. The mixture was evaporated and the residue was partitioned between diethyl ether and water. The aqueous layer was acidified to pH2 by the addition of 2N hydrochloric acid solution and extracted with diethyl ether. The organic phase was washed with brine, dried (MgSO$_4$) and evaporated. There was thus obtained 2-[5-fluoro-3-(naphth-2-ylthio)phenyl]-2-hydroxybutyric acid (4.8 g, 83%), m.p. 133° C. (recrystallised from toluene).

After repetition of the above reactions a mixture of the acid so obtained (5.5 g) and (−)-ephedrine (2.6 g) was dissolved in a mixture of diethyl ether (100 ml) and acetone (30 ml) by heating the mixture to reflux. The solution was evaporated. The resultant foam was redissolved in diethyl ether (200 ml). The hot solution was filtered and allowed to stand for 96 hours. The precipitated solid was filtered off. The mother liquors were washed with 2N hydrochloric acid solution, dried (MgSO$_4$) and evaporated. A mixture of the residue so obtained (3.2 g) and (+)-ephedrine was dissolved in diethyl ether (200 ml). The hot solution was filtered and allowed to stand for 72 hours. The precipitated solid was filtered off and dried. The material was dissolved in a mixture of diethyl ether and acetone and the solution was washed with 2N hydrochloric acid solution, dried (MgSO$_4$) and evaporated. There was thus obtained (+)-2-[5-fluoro-3-(naphth-2-ylthio)phenyl]-2-hydroxybutyric acid (1.43 g) as a foam, $[\alpha]^{20} = +27.9$ (chloroform, c=1 g/100 ml).

An excess of a solution of diazomethane in diethyl ether (0.67M) was added to a solution of the (+)-acid so obtained (1.43 g) in diethyl ether (50 ml) and the mixture was stirred at ambient temperature for 15 minutes. Glacial acetic acid (1 drop) was added and the mixture was evaporated. There was thus obtained methyl (+)-2-[5-fluoro-3-(naphth-2-ylthio)phenyl]-2-hydroxybutyrate (1.4 g), $[\alpha]^{20} = +32.2$ (chloroform, c=1 g/100 ml).

A solution of the ester so obtained (1.4 g) in diethyl ether (20 ml) was added dropwise to a stirred suspension of lithium aluminium hydride (0.215 g) in diethyl ether (20 ml). The mixture was stirred at ambient temperature for 1 hour. Ethyl acetate (1 ml) and water (2 ml) were added in turn, the mixture was filtered and the filtrate was evaporated. There was thus obtained the required starting material (1.29 g) as an oil.

NMR Spectrum (CDCl$_3$, δ values) 0.75 (t, 3H), 1.5-2.0 (m, 2H), 3.7 (doublet of doublets, 2H), 6.7-8.0 (m, 10H).

EXAMPLE 5

Using a similar procedure to that described in Example 4, (+)-2-[5-fluoro-3-(naphth-2-ylthio)phenyl]butane-1,2-diol was reacted with pentan-2-one. There was thus obtained: a less polar isomer, (+)-4-ethyl-4-[5-fluoro-3-(naphth-2-ylthio)phenyl]-2-methyl-2-propyl-1,3-dioxolane, in 37% yield as an oil, NMR Spectrum (CDCl$_3$, δ values) 0.75 (t, 3H), 0.95 (t, 3H), 1.2 (s, 3H), 1.4-2.0 (m, 6H), 4.0 (s, 2H), 6.75-7.2 (m, 3H), 7.3-8.0 (m, 7H), $[\alpha]^{20} = +17.2$ (chloroform, c=1 g/100 ml); and a more polar isomer in 25% yield as an oil, NMR Spectrum (CDCl$_3$, δ values) 0.7-0.9 (m, 6H), 1.4 (s, 3H), 1.2-2.0 (m, 6H), 4.0 (q, 2H), 6.75-7.1 (m, 3H), 7.3-8.0 (m, 7H), $[\alpha]^{20} = +11.8$ (chloroform, c=1 g/100 ml).

EXAMPLE 6

Using a similar procedure to that described in Example 4, (+)-2-[5-fluoro-3-(naphth-2-ylthio)phenyl]butane-1,2-diol was reacted with acetaldehyde. There was thus obtained as a 2:1 mixture of diastereoisomers (+)-4-ethyl-4-[5-fluoro-3-(naphth-2-ylthio)phenyl]-2-methyl-1,3-dioxolane in 86% yield as an oil.

NMR Spectrum (CDCl$_3$, δ values) 0.7-0.9 (m, 3H), 1.3-1.6 (m, 3H), 1.7-2.1 (m, 2H), 3.8-4.2 (m, 2H), 5.0-5.4 (m, 1H), 6.75-7.2 (m, 3H), 7.3-8.0 (m, 7H).

EXAMPLE 7

The procedure described in Example 1 was repeated except that 2-[3-(4-tert-butylphenylthio)phenyl]butane-1,2-diol was used in place of 2-[3-(naphth-2-ylthio)-phenyl]butane-1,2-diol. There was thus obtained 4-ethyl-2,2-dimethyl-4-[3-(4-tert-butylphenylthio)-phenyl]-1,3-dioxolane in 17% yield as an oil.

NMR Spectrum (CDCl$_3$, δ values) 0.78 (t, 3H), 1.25 (s, 3H), 1.30 (s, 9H), 1.48 (s, 3H), 1.80 (m, 2H), 4.05 (m, 2H), 7.1-7.35 (m, 8H).

The 2-[3-(4-tert-butylphenylthio)phenyl]butane-1,2-diol used as a starting material was obtained as follows:

Using a similar procedure to that described in the first paragraph of the portion of Example 4 which is concerned with the preparation of starting materials, 4-tert-butylphenylthiol was reacted with 3-iodobromobenzene to give 3-bromophenyl 4-tert-butylphenyl sulphide in 46% yield as an oil.

Using a similar procedure to that described in the second and third paragraphs of the portion of Example 1 which is concerned with the preparation of starting material, 3-bromophenyl 4-tert-butylphenyl sulphide was reacted with 1-(tert-butyldimethylsilyloxy)-butan-2-one and the product so obtained was treated with potassium fluoride. There was thus obtained the required starting material in 36% yield as an oil.

EXAMPLE 8

Using a similar procedure to that described in Example 1, except that 2-[3-(4-tert-butylphenylsulphonyl-phenyl]butane-1,2-diol was used in place of 2-[3-(naphth-2-ylthio)phenyl]butane-1,2-diol, there was obtained 4-ethyl-2,2-dimethyl-4-[3-(4-tert-butylphenylsulphonyl)phenyl]-1,3-dioxolane in 31% yield, m.p. 108°-110° C.

NMR Spectrum (CDCl$_3$, δ values) 0.75 (t, 3H), 1.25 (s, 3H), 1.30 (s, 9H), 1.50 (s, 3H), 1.85 (m, 2H), 4.10 (m, 2H), 7.4-7.6 (m, 4H), 7.78-7.97 (m, 4H).

The 2-[3-(4-tert-butylphenylsulphonylphenyl]butane-1,2-diol used as a starting material was obtained as follows:

3-Bromophenyl 4-tert-butylphenyl sulphide was oxidised with potassium peroxymonosulphate using the procedure described in the first paragraph of the portion of Example 3 which is concerned with the preparation of starting materials. There was thus obtained 3-bromophenyl 4-tert-butylphenyl sulphone in 77% yield as an oil.

Using a similar procedure to that described in the second and third paragraphs of the portion of Example 1 which is concerned with the preparation of starting materials, the product so obtained was reacted with 1-(tert-butyldimethylsilyloxy)butan-2-one and the resultant product was treated with potassium fluoride. There was thus obtained the required starting material in 32% yield as an oil.

EXAMPLE 9

Using a similar procedure to that described in the first paragraph of the portion of Example 1 which is concerned with the preparation of starting materials, 3-biphenylthiol was reacted with 4-(3-bromophenyl)-4-ethyl-2,2-dimethyl-1,3-dioxolane. The material so obtained was purified by column chromatography on reversed-phase silica using decreasingly polar mixtures of methanol and water as eluent. There was thus obtained 4-[3-(3-biphenylylthio)phenyl]-4-ethyl-2,2-dimethyl-1,3-dioxolane in 21% yield as an oil.

NMR Spectrum ($CDCl_3$, δ values) 0.8 (t, 3H), 1.2 (s, 3H), 1.5 (s, 3H), 1.8 (m, 2H), 4.05 (d, 1H), 4.1 (d, 1H), 7.2–7.7 (m, 13H).

The 4-(3-bromophenyl)-4-ethyl-2,2-dimethyl-1,3-dioxolane used as a starting material was obtained as follows:

Using a similar procedure to that described in the second and third paragraphs of the portion of Example 1 which is concerned with the preparation of starting materials 3-bromoiodobenzene was reacted with 1-(tert-butyldimethylsilyloxy)butan-2-one and the resultant product was treated with potassium fluoride. There was thus obtained 2-(3-bromophenyl)butane-1,2-diol in 78% yield as an oil.

Using a similar procedure to that described in Example 1, the product so obtained was reacted with 2,2-dimethoxypropane. There was thus obtained the required starting material in 75% yield as an oil.

NMR Spectrum ($CDCl_3$, δ values) 0.7 (t, 3H), 1.25 (s, 3H), 1.45 (s, 3H), 1.75 (m, 2H), 4.0 (q, 2H), 7.0–7.4 (m, 4H).

EXAMPLE 10

The following illustrate representative pharmaceutical dosage forms containing the compound of formula I, or a pharmaceutically-acceptable salt salt thereof (hereafter compound X), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 mg |
| Lactose Ph. Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid | |
| (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | mg/ml |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | mg/ml |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | mg/ml |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

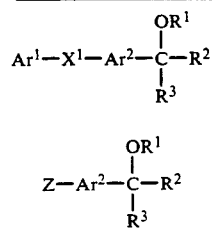

-continued
CHEMICAL FORMULAE

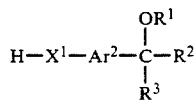
IV

-continued
SCHEME I

III  (i) $R^3Li$ or $R^3MgZ$, THF
(ii) DDQ or $MnO_2$
(iii) $R^2Li$ or $R^2MgZ$, THF;
(iv) BuLi or Mg, THF; $R^2COR^3$, THF
(v) $R^1Z$, base
Note R = (1–4C)alkyl such as Me or Et

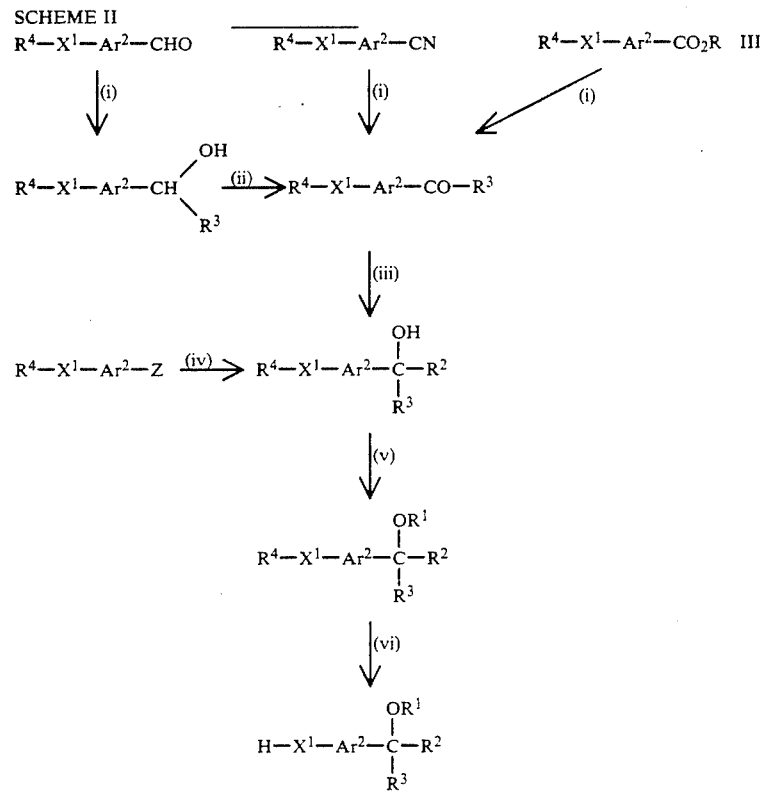

Reagents
(i) to (v) as in Scheme I
(vi) Conventional removal of the protecting group $R^4$ which is, e.g, COMe, THP, $CH_2Ph$ or Me.

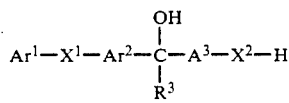

SCHEME I

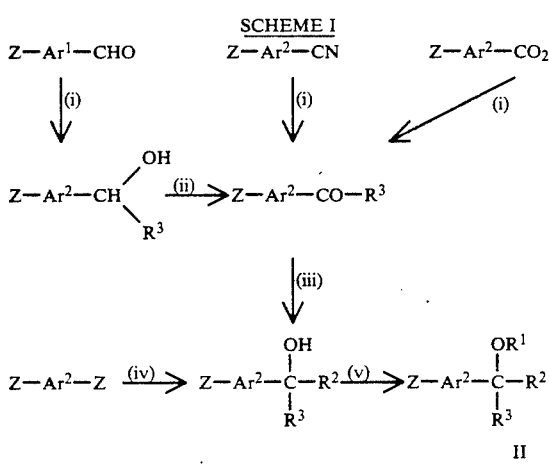

Reagents

What we claim is:

1. A diaryl ether cyclic ether of the formula I

I wherein
Ar$^1$ is phenyl or naphthyl which may optionally bear one or more substituents selected from amino, halogeno, hydroxy, cyano, (1–4C)alkyl, (2–4C)alkenyl, (2–4C)alkynyl, (1–4C)alkoxy, (1–4C)alkylthio, (1–4C)alkylsulphinyl, (1–4C)alkylsulphonyl, (1–4C)alkylamino, di-[(1–4C)alkyl]amino, (1–4C)alkoxycarbonyl, (2–4C)alkanoyl, hydroxy-(1–4C)alkyl, fluoro-(1–4C)alkyl, cyano-(1–4C)alkyl, fluoro-(1–4C)alkoxy, cyano-(1–4C)alkoxy, phenyl and benzoyl, and wherein said phenyl or benzoyl substituents may optionally bear a substituent selected from halogeno, (1–4C)alkyl and (1–4C)alkoxy;
wherein $X^1$ is oxy, thio, sulphinyl or sulphonyl; wherein Ar$^2$ is phenylene which may optionally bear one or two substituents selected from halogeno, hydroxy, amino, nitro, cyano, carbamoyl, (1–4C)alkyl, (3–4C)alkenyloxy, (1–4C)alkoxy, (1–4C)alkylthio, (1–4C)alkylsulphinyl, (1–4C)alkysulphonyl, (1–4C)alkylamino, di-[(1–4C)alkyl]amino, fluoro-(1–4C)alkyl, cyano-(1–4C)alkyl, (1–4C)alkoxycarbonyl, N-[(1–4C)alkyl]carbamoyl, N,N-di-[(1–4C)alkyl]carbamoyl, (2–4C)alkanoylamino, fluoro-(1–4C)alkoxy, cyano-(1–4C)alkoxy, carbamoyl-(1–4C)alkoxy, amino-(2–4C)alkoxy, (1–4C)alkylamino-(2–4C)alkoxy, di-[(1–4C)alkyl]amino-(2–4C)alkoxy and (1–4C)alkoxycarbonyl-(1–4C)alkoxy;

wherein $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 to 7 ring atoms, wherein $A^2$ and $A^3$, which may be the same or different, each is (1–3C)alkylene and $X^2$ is oxy, and which ring may bear one or two substituents, which may be the same or different, selected from halogeno, hydroxy, cyano, (1–4C)alkyl, (1–4C)alkoxy, (1–4C)alkylthio, (1–4C)alkylsulphinyl, (1–4C)alkylsulphony and fluoro-(1–4C)alkyl, and wherein $R^3$ is (1–6C)alkyl, (2–6C)alkenyl, (2–6C)alkynyl, fluoro-(1–4C)alkyl, cyano-(1–4C)alkyl, hydroxy-(1–4C)alkyl, (1–4C)alkoxy-(1–4C)alkyl or (2–4C)alkanoyloxy-(1–4C)alkyl; or a pharmaceutically-acceptable salt thereof.

2. A diaryl ether cyclic ether of the formula I as claimed in claim 1 wherein $Ar^1$ is phenyl, naphth-1-yl or naphth-2-yl which may optionally bear one or two substituents selected from amino, fluoro, chloro, cyano, methyl, tert-butyl, methoxy, methylthio, methylsulphinyl, methylsulphonyl and 2-cyanoprop-2-yl;

$X^1$ is thio, sulphinyl or sulphony;

$Ar^2$ is 1,3-phenylene or 1,4-phenylene which may optionally bear one substituent selected from fluoro, hydroxy, amino, nitro, methoxy, methylamino, cyanomethoxy and trifluoromethyl;

$R^1$ and $R^2$ together form a group of the formula —$A^2$—$X^2$—$A^3$— which together with the oxygen atom to which $A^2$ is attached and with the carbon atom to which $A^3$ is attached, defines a ring having 5 or 6 ring atoms, wherein $A^2$ is methylene or ethylene, $A^3$ is methylene and $X^2$ is oxy, and which ring may bear one or two substituents selected from fluoro, methyl, methoxy and trifluoromethyl, and $R^3$ is methyl or ethyl;

or a pharmaceutically-acceptable salt thereof.

3. A diaryl ether cyclic ether of the formula I as claimed in claim 1 wherein $Ar^1$ is phenyl or naphth-2-yl which may optionally bear one or two substituents selected from fluoro, chloro, methyl, ethyl, isopropyl, tert-butyl, methoxy, trifluoromethyl, 2-cyanoprop-2-yl, phenyl and benzoyl and wherein said phenyl or benzoyl substituents may optionally bear a substituent selected from chloro, methyl and methoxy;

$X^1$ is oxy, thio, sulphinyl or sulphonyl;

$Ar^2$ is 1,3-phenylene which may optionally bear a substituent selected from fluoro, chloro, bromo and trifluoromethy;

$R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 or 6 ring atoms, wherein $A^2$ and $A^3$, which may be the same or different, each is methylene or ethylene and $X^2$ is oxy, and which ring may bear one or two substituents selected from methyl, ethyl, propyl and isopropyl, and $R^3$ is methyl or ethyl;

or a pharmaceutically-acceptable salt thereof.

4. A diaryl ether cyclic ether of the formula I as claimed in claim 1 wherein $Ar^1$ is phenyl which may optionally bear a substituent selected from fluoro, methyl, tert-butyl and phenyl; or $Ar^1$ is naphth-2-yl;

$X^1$ is thio, sulphinyl or sulphonyl;

$Ar^2$ is 1,3-phenylene which may optionally bear a substituent selected from fluoro, chloro, bromo and trifluoromethyl;

$R^1$ and $R^2$ together form a group of the formula —$A^2$—$X^2$—$A^3$ which, together with the oxygen atom to which $A^2$ is attached and with the carbon atom to which $A^3$ is attached, defines a ring having 5 ring atoms, wherein each of $A^2$ and $A^3$ is methylene and $X^2$ is oxy, and which ring may bear one or two substituents selected from methyl, ethyl and propyl, and $R^3$ is methyl or ethyl;

or a pharmaceutically-acceptable salt thereof.

5. A diaryl ether cyclic ether of the formula I as claimed in claim 1 wherein $Ar^1$ is 4-tert-butylphenyl or naphth-2-yl;

$X^1$ is thio;

$Ar^2$ is 1,3-phenylene or 5-fluoro-1,3-phenylene;

$R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 ring atoms, wherein each of $A^2$ and $A^3$ is methylene and $X^2$ is oxy, and which ring bears on $A^2$ two substituents, which may be the same or different, selected from methyl, ethyl and propyl;

or a pharmaceutically-acceptable salt thereof.

6. A diaryl ether cyclic ether of the formula I, or a pharmaceutically-acceptable salt thereof, selected from the group consisting of:

4-ethyl-2,2-dimethyl-4-[3-(naphth-2-ylthio)phenyl]-1,3-dioxolane, 4-ethyl-2,2-dimethyl-4-[3-(4-tert-butylphenylthio)phenyl]-1,3-dioxolane, (+)-2,4-diethyl-4-[5-fluoro-3-(naphth-2-ylthio)phenyl]-2-methyl-1,3-dioxolane (the more polar isomer) and (+)-4-ethyl-4-[5-fluoro-3-(naphth-2-ylthio)phenyl]-2-methyl-2-propyl-1,3-dioxolane (the more polar isomer).

7. A pharmaceutical composition which comprises a a 5-lipoxygenase inhibitory amount of a cyclic ether of the formula I, or a pharmaceutically-acceptable salt thereof as claimed in any one of claims 1 to 6, in association with a pharmaceutically-acceptable diluent or carrier.

8. A method of treating a disease or medical condition mediated alone or in part by one or more leukotrienes which comprises administering to a warm-blooded animal requiring such treatment an effective amount of a diaryl ether cyclic ether of the formula I, or a pharmaceutically-acceptable salt thereof, as claimed in any one of claims 1 to 6.

* * * * *